US00PP15400P3

(12) United States Plant Patent
Lim et al.

(10) Patent No.: US PP15,400 P3
(45) Date of Patent: Dec. 7, 2004

(54) SHRUB ROSE PLANT NAMED BAIHERO

(50) Latin Name: *Rosa hybrida*
Varietal Denomination: BAIhero

(75) Inventors: Peter P. Lim, Yamhill, OR (US); Jerry Twomey, Leucadia, CA (US)

(73) Assignee: Bailey Nurseries, Inc., St. Paul, MN (US)

( * ) Notice: Subject to any disclaimer, the term of this patent is extended or adjusted under 35 U.S.C. 154(b) by 78 days.

(21) Appl. No.: 10/385,623

(22) Filed: Mar. 12, 2003

(65) Prior Publication Data

US 2004/0199966 P1 Oct. 7, 2004

(51) Int. Cl.[7] ..... A01H 5/00
(52) U.S. Cl. ..... Plt./108

(58) Field of Search ..... Plt./108, 102, 149, Plt./150, 151

*Primary Examiner*—Howard J. Locker
(74) *Attorney, Agent, or Firm*—Burns, Doane, Swecker & Mathis, L.L.P.

(57) ABSTRACT

A new and distinct variety of Landscape Shrub rose plant is provided which abundantly forms on a substantially continuous basis double blossoms that display a bright medium red coloration. The blossoms also display a light fragrance similar to mild honey. The plant exhibits a vigorous, compact and bushy growth habit, and forms attractive foliage that commonly possesses a tint of red-purple when young and assumes a satiny medium green coloration when mature. Good resistance to Blackspot and Powdery Mildew is displayed. The foliage coloration contrasts nicely with the bright medium red blossom coloration. The new variety is particularly well suited for growing as attractive ornamentation in parks and gardens.

1 Drawing Sheet

Botanical/commercial classification: *Rosa hybrida*/Landscape Shrub Rose Plant.
Varietal denomination: cv. 'BAIhero'.

SUMMARY OF THE INVENTION

The new variety of *Rosa hybrida* Landscape Shrub rose plant was creaated at Yamhill, Oreg., U.S.A., during 1993 by artificial pollination wherein two parents were crossed which previously had been studied in the hope that they would contribute the desired characteristics. The female parent (i.e., the seed parent) was an unnamed seedling (non-patented in the United States) from the breeding program. The male parent (i.e., the pollen parent) was the 'Lillian Gibson' variety (non-patented in the United States). The parentage of the new variety can be summarized as follows:

Unnamed Seedling×'Lillian Gibson'.

The seeds resulting from the above pollination were sown and plants were obtained which were physically and biologically different from each other. Selective study resulted in the identification of a single plant of the new variety having the distinctive ornamental characteristics hereafter described.

It was found that the new variety of the present invention:

(a) exhibits a vigorous, compact and bushy growth habit, (b) abundantly forms on a substantially continuous basis attractive mildly fragrant double blossoms commonly having a diameter of approximately 7 cm that display a bright medium red coloration, (c) forms attractive foliage that commonly possesses a tint of red-purple when young and assumes a satiny medium green coloration when mature, (d) displays good resistance to Blackspot and Powdery Mildew, and (e) is particularly well suited for growing as attractive ornamentation in parks and gardens.

The new variety of the present invention can be readily distinguished from its 'Lillian Gibson' parental variety. More specifically, the 'Lillian Gibson' variety forms rose-pink blossoms having approximately 40 petals, and the new variety displays bright medium-red blossoms having approximately 23 petals on average.

The new variety well meets the needs of the horticultural industry and can be grown to advantage in the landscape where attractive ornamentation is desired. The distinctive bright medium red blossoms are displayed throughout the summer. The plant can be grown as a specimen or as a mass planting.

The new variety has been found to undergo asexual propagation by budding on an understock and by the rooting of cuttings. Asexual propagation by budding onto 'Dr. Huey' rootstock (non-patented in the United States) first conducted during April 1994 at Yamhill, Oreg., U.S.A., and subsequently by the rooting of cuttings at Phoenix, Ariz., U.S.A., has shown that the characteristics of the new variety are stable and are strictly transmissible by such asexual propagation from one generation to another.

Initially the new plant was designated 93A254-1. The new variety subsequently has been named the 'BAIhero' variety, and is being marketed while using the MY HERO trademark.

BRIEF DESCRIPTION OF THE PHOTOGRAPHS

The accompanying photographs show as nearly true as it is reasonably possible to make the same in a color illustrations of this character, typical specimens of the new variety. The rose plants of the new variety had been propagated by the rooting of cuttings, were approximately two years of age, and were being grown outdoors at St. Paul, Minn., U.S.A.

DETAILED DESCRIPTION

Figure 1:
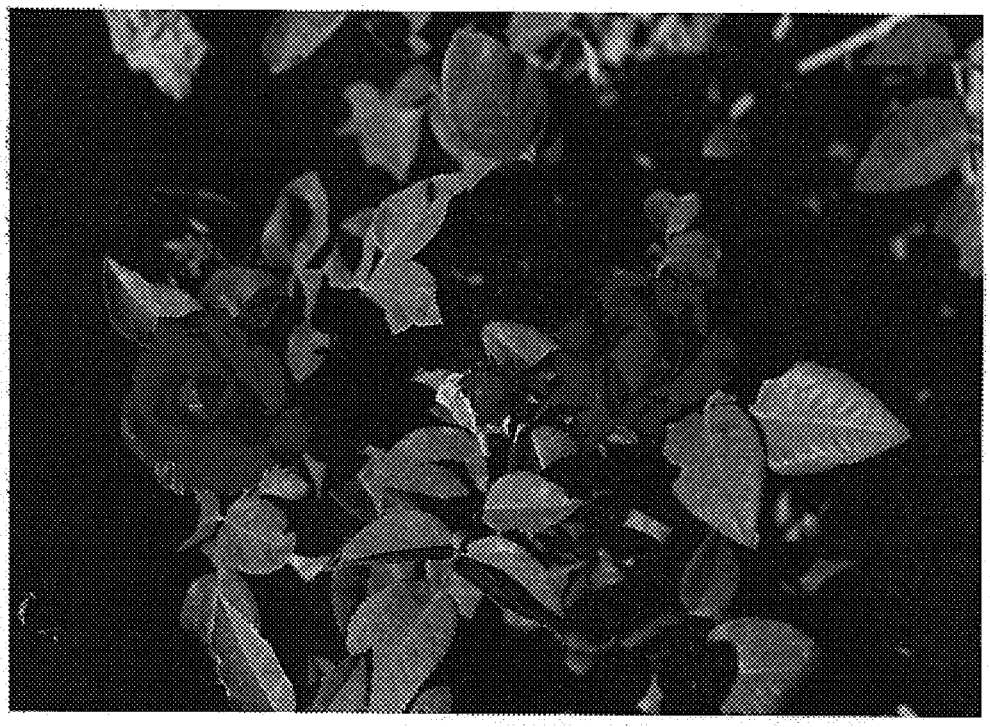
FIG. 1 illustrates typical blossoms and foliage of the new variety while growing in the landscape during the summer. The attractive satiny medium green foliage is shown.
Figure 2:
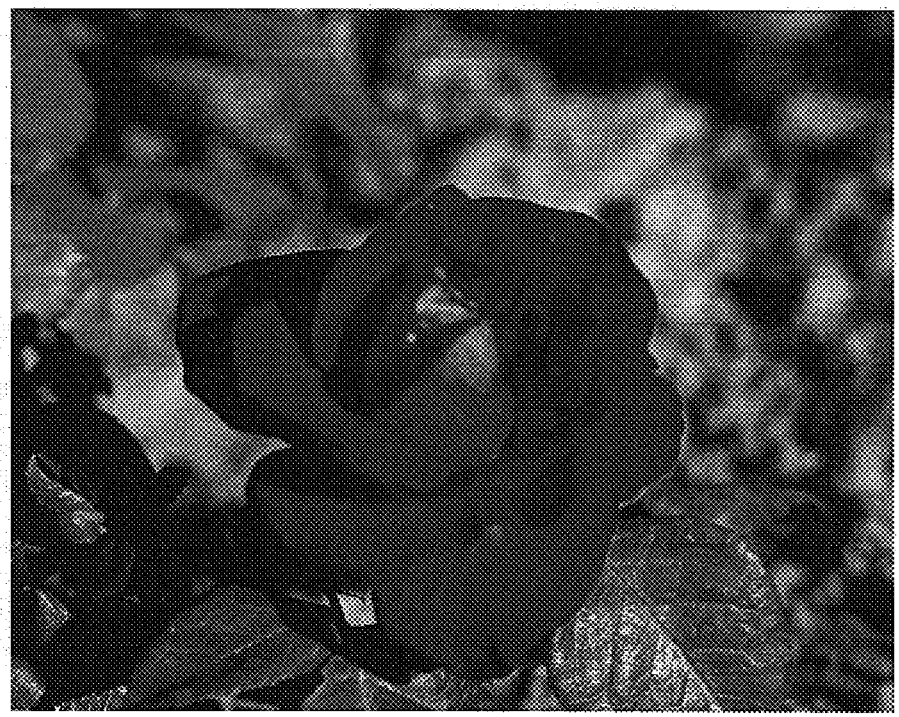
FIG. 2 illustrates a closer view of a bright red blossom and satiny medium green foliage. To the left of the blossom some new foliage having a tint of red-purple coloration is shown.

The chart used in the identification of the colors is that of The Royal Horticultural Society (R.H.S. Colour Chart). Common color terms are to be accorded their ordinary dictionary significance. The description is based on the observation of two and three year-old plants while growing on their own roots outdoors during June and July at St. Paul, Minn., U.S.A., and during October at Phoenix, Ariz., U.S.A.

Botanical classification: *Rosa hybrida*, var. 'BAIhero'.
Class: Landscape Shrub Rose.
Plant:
- *Height.*—Approximately 90 cm on average at the end of the growing season.
- *Width.*—Approximately 80 to 90 cm on average at the end of the growing season.
- *Habit.*—Substantially round and bushy.

Branches:
- *Color.*—Young stems: near Yellow-Green Group 144B with some highlights of Red Group 53A. Adult wood: Yellow-Green Group 144A.
- *Thorns.*—Size: commonly approximately 0.75 cm in length on average with some smaller bristles/prickles near the peduncle. Color: commonly between Greyed-Purple Group 184C and 184D.

Leaves:
- *Stipules.*—Generally parallel with the auricle facing outward.
- *Petioles.*—Upper surface: Yellow-Green Group 144A with highlights of Greyed-Purple Group 184A and commonly bear some small prickles. Under surface: Yellow-Green Group 144C.
- *Leaflets.*—Number: 3, 5, and 7 (most often). Shape: ovate with a rounded base and an acuminate tip. Serration: finely serrate. Texture: leathery. General appearance: light to medium green with a satin finish. Color (young foliage): Upper surface: Greyed-Purple Group 185A with highlights of Green Group 143B. Under surface: Greyed-Purple Group 187C with highlights of Green Group 141C. Color (adult foliage): Upper surface: commonly between Green Group 137B to Green Group 137C. Under surface: Yellow-Green Group 147B with some presence of Green Group 138B.

Inflorescence:
- *Number of flowers.*—Commonly in clusters of three per stem.
- *Peduncle.*—With some prickles, medium green, commonly Yellow-Green Group 144B in coloration, and the length in approximately 5 cm on average.
- *Sepals.*—Upper surface: between Yellow-Green Group 146B and 146C in coloration. Under surface: Yellow-Green Group 147A with areas of White Group 155D, and some pubescence. Size: approximately 2.5 cm in length with some extensions.
- *Buds.*—Shape: rounded. Size: small to medium. Length: approximately 2 cm on average. Diameter: approximately 2.75 cm on average. Color: Upper surface: commonly between Red Group 45B and Cardinal Red, Red Group 53B. Under surface: Red Group 53D blended with Red Group 53B and 53C. Basal petal spot: Yellow-Green Group 154B.
- *Flower.*—Shape: double. Diameter: approximately 7 cm on average. Color (when opening begins): Upper surface: Cardinal Red, between Red Group 53B and 53C. Under surface: Crimson, Red Group 52C. Color (when blooming): Upper surface: between Cardinal Red, Red Group 53C, and Spinel Red, Red Group 54B. Under surface: Spinel Red, Red Group 54B, with highlights of Cardinel Red, Red Group 53C. Color (end of blooming): Upper surface: between Cardinal Red, Red Group 53C, and Spinel Red, Red Group 54A. Under surface: Spinel Red, Red Group 54A, with highlights of Red Group 53D. Basal petal spot: Green-White Group 157A. Fragrance: similar to mild honey. Lasting quality: the blossoms commonly last approximately 3 to 5 days from bud on the plant on average depending upon the temperature, and the level of sunlight. Petal number: approximately 23 on average under normal growing conditions. Petal shape: wedge-shaped commonly with a curled apex when fully open. Petal drop: the petals drop easily. Stamen number: approximately 68 on average. Anthers: Greyed-Yellow Group 162B in coloration. Filaments: Red Group 47A with highlights of Yellow Group 11A in coloration. Pistils: approximately 72 on average. Stigmas: Yellow Group 2A in coloration. Styles: Red Group 43B in coloration. Receptacle: separate and free. Hips: ovoid in configuration, approximately 1 cm in length, and approximately 0.75 cm in width. Seeds: dark brown in coloration, and approximately 2 mm in length.

Development:
- *Vegetation.*—Vigorous.
- *Blooming.*—Substantially everblooming.
- *Resistance to diseases.*—Good resistance to Blackspot, and Powdery Mildew.
- *Aptitude to bear fruit.*—Good.
- *Hardiness zone.*—Zone Nos. 4 to 7.

We claim:

1. A new and distinct variety of Landscape Shrub rose plant characterized by the following combination of characteristics:

(a) exhibits a vigorous, compact and bushy growth habit, (b) abundantly forms on a substantially continuous basis attractive mildly fragrant double blossoms commonly having a diameter of approximately 7 cm that display a bright medium red coloration, (c) forms attractive foliage that commonly possesses a tint of red-purple when young and assumes a satiny medium green coloration when mature, (d) displays good resistance to Blackspot and Powdery Mildew, and (e) is particularly well suited for growing as attractive ornamentation in parks and gardens;

substantially as herein shown and described.

* * * * *